US012564338B2

(12) United States Patent
Boukhayma

(10) Patent No.: US 12,564,338 B2
(45) Date of Patent: Mar. 3, 2026

(54) NON-INVASIVE GLUCOSE SENSOR

(71) Applicant: ECOLE POLYTECHNIQUE FEDERALE DE LAUSANNE (EPFL), Lausanne (CH)

(72) Inventor: Assim Boukhayma, Neuchâtel (CH)

(73) Assignee: ECOLE POLYTECHNIQUE FEDERALE DE LAUSANNE (EPFL), Lausanne (CH)

( * ) Notice: Subject to any disclaimer, the term of this patent is extended or adjusted under 35 U.S.C. 154(b) by 694 days.

(21) Appl. No.: 17/312,228

(22) PCT Filed: Sep. 9, 2019

(86) PCT No.: PCT/IB2019/057576
§ 371 (c)(1),
(2) Date: Jun. 9, 2021

(87) PCT Pub. No.: WO2020/121073
PCT Pub. Date: Jun. 18, 2020

(65) Prior Publication Data
US 2022/0022784 A1 Jan. 27, 2022

(30) Foreign Application Priority Data

Dec. 14, 2018 (CH) ..................................... 01546/18

(51) Int. Cl.
*A61B 5/145* (2006.01)
*A61B 5/00* (2006.01)
*A61B 5/1455* (2006.01)
(52) U.S. Cl.
CPC ...... *A61B 5/14532* (2013.01); *A61B 5/14546* (2013.01); *A61B 5/1455* (2013.01); *A61B 5/6824* (2013.01); *A61B 5/6826* (2013.01)

(58) Field of Classification Search
None
See application file for complete search history.

(56) References Cited

U.S. PATENT DOCUMENTS

2012/0203114 A1    8/2012  Bechtel et al.
2016/0097716 A1*   4/2016  Gulati .................. A61B 5/1495
                                                                 250/340
(Continued)

FOREIGN PATENT DOCUMENTS

EP       3 056 141 A1      8/2016
GB         2494622    *    3/2013
(Continued)

OTHER PUBLICATIONS

Machine Translation of WO-2016117520-A1, Patent Translate, pp. 1-20, printed on Jul. 28, 2024 (Year: 2016).*
(Continued)

*Primary Examiner* — Jennifer Robertson
*Assistant Examiner* — Om Patel
(74) *Attorney, Agent, or Firm* — HoustonHogle LLP

(57) ABSTRACT

An optical device for the in noninvasive determination of the concentration of glucose or another analyte in blood using a combination of Raman spectrometry and PPG. The device includes an optical detector, preferably a CMOS imager including pinned photodiodes (PPD) to collect a time-variable signal and a logic circuit arranged to determine a glucose concentration based on variations in the optical signal happening in a frequency range compatible with the cardiac rhythm.

26 Claims, 4 Drawing Sheets

(56) References Cited

U.S. PATENT DOCUMENTS

| | | | | |
|---|---|---|---|---|
| 2016/0242657 A1 * | 8/2016 | Wang | .................. | A61B 5/0261 |
| 2017/0231500 A1 * | 8/2017 | Rothberg | ........... | A61B 5/14532 |
| | | | | 250/459.1 |
| 2020/0163597 A1 * | 5/2020 | Dalvi | .................. | A61B 5/0066 |

FOREIGN PATENT DOCUMENTS

| | | | | |
|---|---|---|---|---|
| JP | H10501995 A | 2/1998 | | |
| JP | 2016-508777 | 3/2016 | | |
| JP | 2017504362 A | 2/2017 | | |
| KR | 10-2011-0094405 | 8/2011 | | |
| WO | WO-9736540 A1 * | 10/1997 | ......... | A61B 5/14532 |
| WO | WO-0033065 A1 * | 6/2000 | ......... | A61B 5/14532 |
| WO | WO-2008068685 A1 * | 6/2008 | ........... | A61B 5/0066 |
| WO | WO 2012136982 | 10/2012 | | |
| WO | WO 2014122126 A1 | 8/2014 | | |
| WO | WO-2015000997 A1 * | 1/2015 | ......... | A61B 5/14532 |
| WO | WO-2016117520 A1 * | 7/2016 | ......... | A61B 5/14532 |
| WO | WO-2016193048 A1 * | 12/2016 | ......... | A61B 5/02416 |
| WO | WO-2018025199 A1 * | 2/2018 | ............... | A61B 5/01 |

OTHER PUBLICATIONS

International Preliminary Report on Patentability, mailed on Jun. 24, 2021, from International Application No. PCT/IB2019/057576, filed on Sep. 9, 2019. 8 pages.

Golparvar, A., et al., "Very Selective Detection of Low Physiopathological Glucose Levels by Spontaneous Raman Spectroscopy with Univariate Data Analysis," BioNanoScience, 11: 871-877 (2021).

Lioe, D., et al., "A CMOS Image Sensor Using High Speed Lock-In Pixels for Stimulated Raman Scattering," Progress in Biomedical Optics and Imaging, 9720: 97200J-1-97200J-7 (2016).

Mars, K., et al., "A Stimulated Raman Scattering Imager Using High-Speed Lateral Electric Fields Modulator and Lock-In Pixels Amplifiers," Visual Communications and Image Processing, 9022: 90220D-1-90220D-8 (2014).

International Search Report and Written Opinion of the International Searching Authority, mailed on Dec. 9, 2019, from International Application No. PCT/IB2019/057576, filed on September 9, 2019. 14 pages.

Korean Office Action issued on Aug. 1, 2024 from Korean Application No. 10-2021-7021275 filed Jul. 7, 2021. 20 pages.

* cited by examiner

NON-INVASIVE GLUCOSE SENSOR

RELATED APPLICATIONS

This application is a § 371 National Phase Application of International Application No. PCT/IB2019/057576, filed on Sep. 9, 2019, now International Publication No. WO 2020/121073 A1, published on Jun. 18, 2020, which International Application claims priority to Swiss Application 01546/18, filed on Dec. 14, 2018, both of which are incorporated herein by reference in their entirety.

FIELD OF THE INVENTION

The present invention concerns a non-invasive device for the in-vivo determination of a concentration of an analyte in blood and, in preferred embodiments, a non-invasive sensor for determining blood glucose level in humans.

DESCRIPTION OF RELATED ART

Glycaemia, the amount of glucose circulating in blood plasma, is the most important clinical parameter in management, diagnostics, and prevention of diabetes, hypoglycaemia, and other metabolic disorders. It is generally recognized that a proper diabetes therapy should aim at maintaining the glucose level in the blood at a value close to normal for as much of the time as possible. Since alimentation, stress, exercise, and other events have a strong influence on glucose blood level, frequent measurements of glycaemia are essential in diabetes management.

Glycaemia is only an example of a clinical parameter tied to a blood concentration. In diabetes therapy alone, other sugars, as well as the glucose fraction tied to the blood proteins are highly significant. Other analytes that are routinely measured in blood include oxygen, $CO_2$, electrolytes, proteins, nitrogenous substances, nutrients, fats, cholesterol, and others.

Existing blood glucose meter require the extraction of a small drop of blood by pricking a fingertip with a lancet. Since a diabetes patient may have to determine its sugar level several times per day, this is clearly highly undesirable and spurred the development of non-invasive, techniques for measuring the blood concentration of glucose and other metabolites. Despite that, non-invasive in vivo measurement of clinically significant analytes in blood remains a challenge.

Many optical measurement techniques have been investigated in the attempt of developing portable meters for glucose or other analytes in blood. These include absorption spectroscopy (particularly in the infrared spectrum), elastic scattering and various types of Raman (inelastic) scattering. Despite many efforts, it is still difficult to obtain, by these means, a measurement sufficiently precise for clinical use.

It is known to measure quantitatively the concentration of various analytes in a sample by Raman scattering in laboratory samples. These techniques require, as a rule, a calibration with standard solutions of known concentration.

Instruments capable of detecting a glucose peak in a Raman spectrum from in vivo measurements are known. A reliable method of processing these spectra to obtain a measure of the glycaemia of clinical value is still lacking, among others due to the absence of a conventional calibration, especially because the condition of illumination and the optical properties of the investigated tissue can vary largely from one subject to another and from one position to another.

Photoplethysmography (PPG) is an optical technique used to detect a cardiac rhythm by observing the changes in light absorption in an irrorated tissue, for example in skin. Such techniques are used in personal exercise monitors, among others.

Several known types of photon detectors are used in Raman spectroscopy and PPG, including p-n junction photodiodes, p-i-n photodiodes (also known as PIN diodes), single photon avalanche diodes (SPAD), photomultipliers and microchannel plates.

Solid-state image sensors are used widely in cell-phones, cameras and scientific imaging devices. In these devices, the conversion of light into an electric signal is performed by an array of pinned photodetectors (PPD, not to be confused with PIN diodes), each PPD has a buried potential well region into which the photoelectron generated by impinging light can be integrated for a desired time, and a transfer gate that can be opened to transfer the integrated charge into a sense node. CMOS image sensor typically include some form of amplification in each pixel, often a source-follower transistor.

BRIEF SUMMARY OF THE INVENTION

The present invention proposes an optical device for determination of the concentration of an analyte in blood that overcomes the limitation of the prior art in that it provides a reliable measurement noninvasively, and preferably continuous.

According to the invention, these aims are achieved by means of the appended claims.

The present disclosure describes in detail the preferred case in which the glycaemia is determined by Raman spectroscopy, but the invention can in fact be extended to the determination of the concentration of other analytes in blood, either by Raman spectroscopy, by fluorescence, absorption spectroscopy, or by any other suitable optical analytical technique.

BRIEF DESCRIPTION OF THE DRAWINGS

The invention will be better understood with the aid of the description of an embodiment given by way of example and illustrated by the figures, in which.

DETAILED DESCRIPTION OF POSSIBLE EMBODIMENTS OF THE INVENTION

Figure 1A:
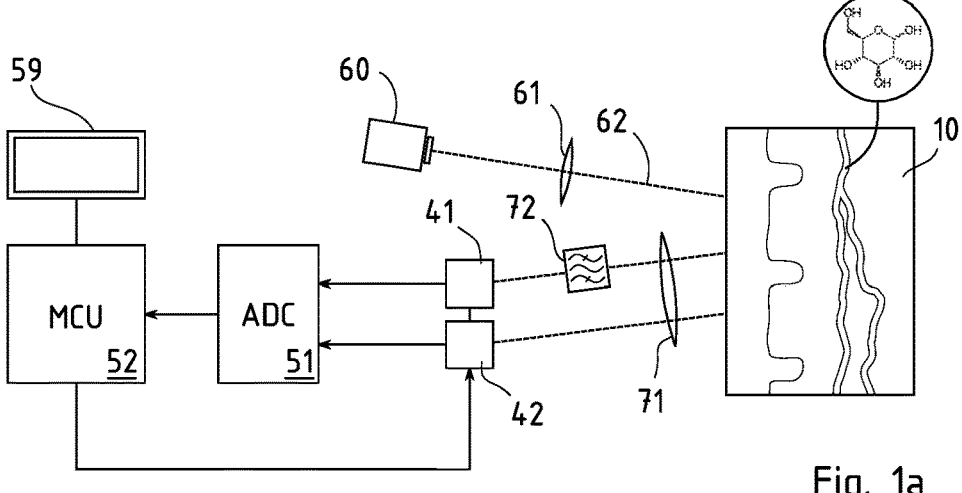
FIGS. 1*a* and 1*b* show schematically and in simplified fashion, a possible structure of an optical device according to the invention.

FIG. 1a illustrates, in a simplified schematic fashion, a device according to an aspect of the invention. The device has an optical interface, not represented, that can be applied to a vascularized part of the body, such as the skin of a finger or of the wrist, to probe the tissue with optical radiation, collect and measure the backscattered light.

In the represented example, the excitation source 60 is used, with a suitable optical device 61, to direct a beam of light 62 into the tissue 10. Preferably, the source 60 will have a narrow spectrum of emission and may be a solid-state laser, for example a VCSEL laser. The emission of the source 60 may be centred in the near UV, visible, near-infrared or mid-infrared regions of the electromagnetic spectrum.

The device of the invention is arranged to collect the optical radiation scattered back from the sample 10. Preferably, a light collection device 71 is used to increase the intensity of the received light on the detectors. Since the light emerging from the sample 10 is not collimated, a non-imaging collector such as a mirror may be used advantageously to send more light on the detectors 41 and 42.

In other variants, the light collection device 71 may be an imaging objective, and the detector 41 an image-sensing array. Such a realization would be capable not only of detecting and measuring the concentration of an analyte, but also of showing its distribution on an image.

According to the present embodiment, at least part of the scattered light received from the sample 10 is filtered by an optical band-pass or monochromator filter 72 that lets pass essentially only the wavelengths in a region of interest, which is chosen to select the characteristic Raman radiation expected from the searched analyte.

Figure 2:
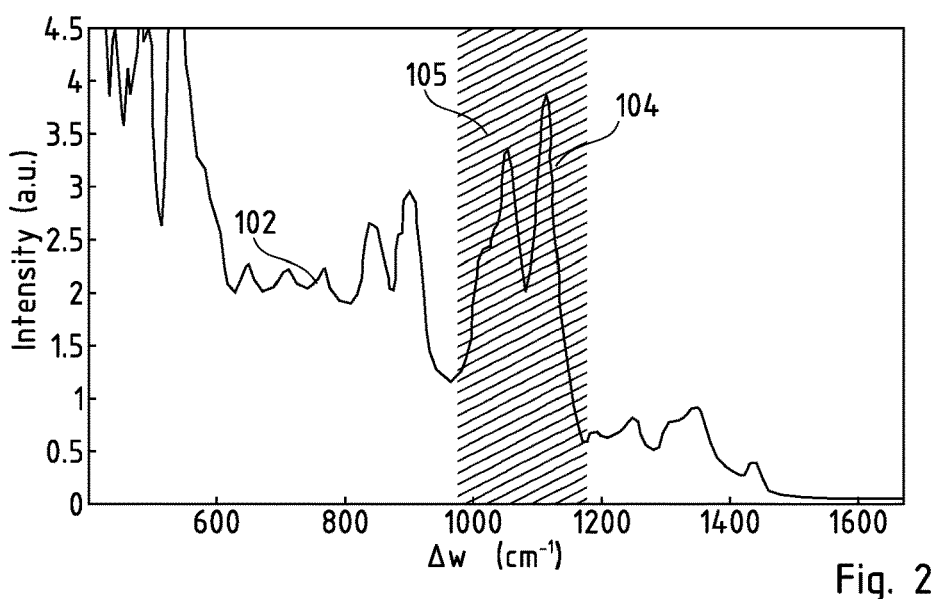
FIG. 2 is a plot of the expected Raman spectrum of light scattered from a sense region of the body, such as the skin of a finger or or of the wrist.

FIG. 2 illustrates the spectrum of the light scattered from a sample containing glucose. The plot reports the intensity of the light, against the shift $\Delta W=1/\lambda_0-1/\lambda_1$, where $\lambda_0$ and $\lambda_1$ denote the wavelengths of the excitation and scattered light, respectively. The spectrum presents a continuous background and several peaks, deriving from the inelastic (Raman) scattering of the excitation light on various molecules. The double peak 104 reveals the presence of glucose. The hashed area 105 is the region of interest selected by the monochromator 72.

A non-represented mode of realization of the invention may include, in lieu of the monochromator filter 72 a dispersive device, like a grating or a spectrometer, and would be arranged to reconstruct the profile of the Raman spectrum 102, rather than its intensity in a region of interest. This variant can detect and measure several analytes at the same time, discriminating them by their specific peaks and signatures in the Raman spectrum. It may also allow to estimate and subtract the continuous background component, thus improving the precision of the measure.

In another variant of the invention, the light source 60 may be a tuneable narrowband source, such as a tuneable laser, or combine several individually selectable fixed-wavelength narrowband sources. Modifying the wavelength of the source amounts to shifting the spectrum 102 of FIG. 2 while keeping still the window 105 defined by the mono-chromator 72, such that the invention can detect different analytes, revealed by different peaks at various wavelengths. VCSEL laser with micromechanical movable mirrors may be advantageously used in this variant, although any suitably compact tuneable source would be applicable.

In another variant the monochromator 72 could be tuneable, thus allowing to select the characteristics emission peaks of several analytes, while keeping the wavelength of the emission source 60 constant. MEMS tuneable Fabry-Perot filters and other optical devices may be employed to this purpose.

The Raman scattering discussed above is a spontaneous process and the resulting radiation is weak. Detection of the characteristic glucose peak requires selective optical filters to attenuate the elastically-scattered radiation, and sensitive photodetectors. The precision of the technique can be improved by adopting the high-performance detector devices that will be described further on, and by enhancing the amplitude of the signature peaks over the background. Stimulated Raman scattering (SRS) and coherent Raman scattering (CARS/CSRS) are physical processes that use several laser beams to generate a resonantly-enhanced Raman signal. Other amplification mechanisms are known and could be incorporated in the present invention.

In an embodiment, the invention also comprises a photoplethysmography device generating a time-variable PPG signal indicative of the amount of blood present at any instant in the sensed region of the body. This technique is also based on the detection of the light scattered from the sensed region of the body 10 and consists in finding an approximately periodic component in the intensity that corresponds to the volume of blood present in the sensed region at any given instant. This component is in phase with the cardiac rhythm and is used in personal exercise monitors, among others, for measuring the heart's activity.

Figure 3:
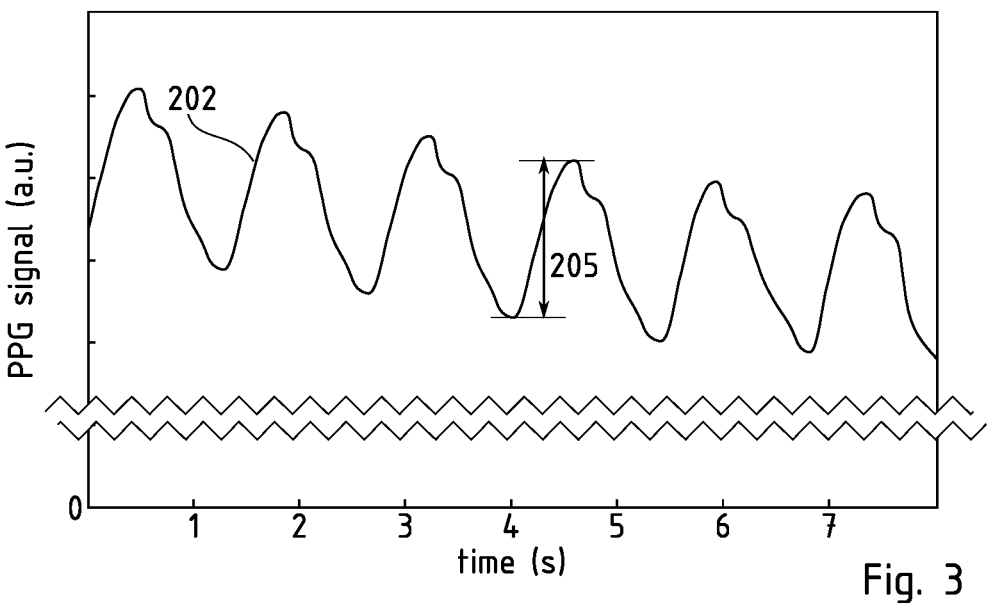
FIG. 3 is a Photoplethysmography (PPG) signal showing the variation of blood volume in the sense region.

FIG. 3 plots the light intensity as a function of the time as collected in a typical PPG apparatus. The PPG signal 202 is characterized by a frequency compatible with the expected heart rhythm. It sits atop a slowly-variable background and is always accompanied by noise and disturbances of various nature, not represented here for clarity. Disturbances and noise may be due to electronic limitations, movements of the subject, and other causes, and can easily overwhelm the PPG signal. Several signal processing techniques can be used to extract the PPG signal 202 from these unwanted effects.

Returning to FIG. 1, the output of both detectors 41 and 42 are digitized by the ADC 51 and processed by logical circuit 52, which could be a microcontroller unit, to determine the concentration of the analyte in blood in the sense region based on the Raman signal from the sensor 41 and on the PPG signal from the sensor 42.

Figure 1B:
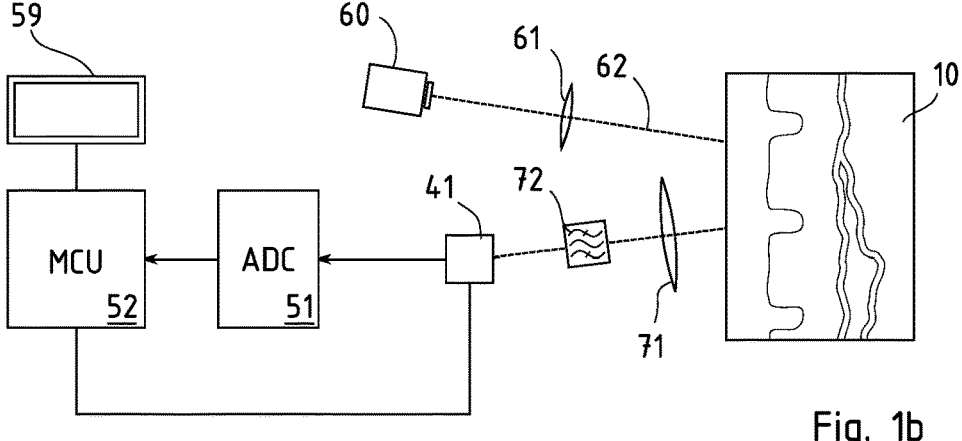

In this example of realization of the invention, the PPG signal derives from a specific photodetector 42, separate from the Raman detector 41. Since the light sensed by the PPG detector 42 is not filtered by the monochromator 72, the PPG detector 42 works on the elastically-scattered light, whose intensity is much higher than the Raman radiation. This is advantageous because it yields a higher signal, but in variants of the invention a single photosensor sensor 41 produces a time-variable Raman signal. FIG. 1b shows a possible arrangement without a distinct optical PPG detector: the processor unit 52 is programmed to detect a component of the Raman signal that varies in a manner compatible with the cardiac rhythm. This component is associate with the concentration of glucose in the pulsatile fraction of the blood in the illuminated region.

In this embodiment the PPG photodetector is sensitive to light emitted from the source 60 and elastically scattered from the sample 10, The invention may include as well as variants with a distinct light source for the PPG sensor.

Figure 4:
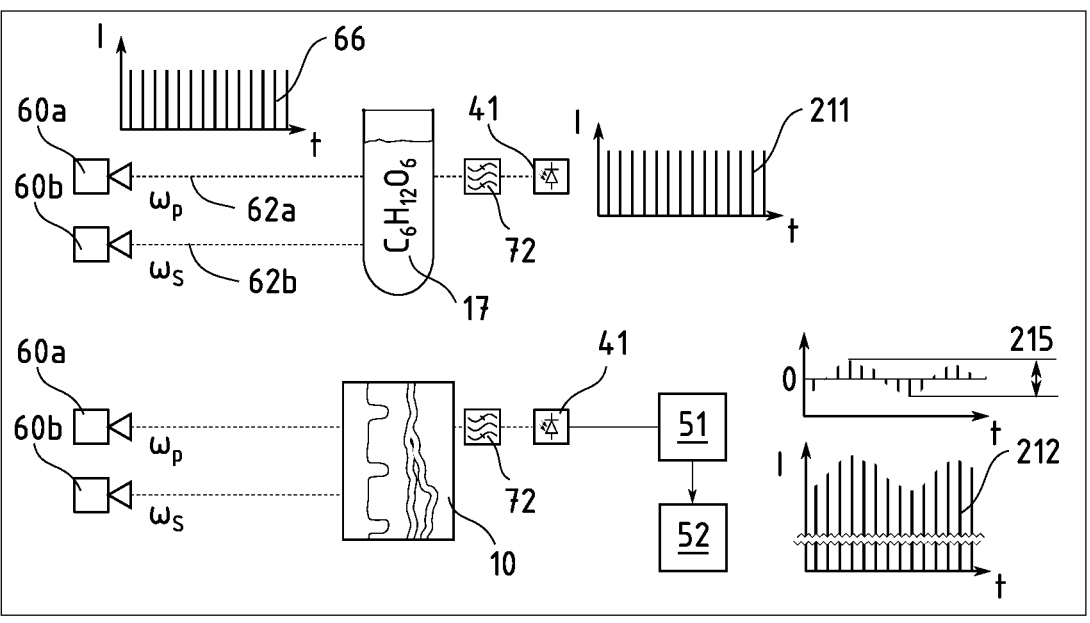
FIG. 4 shows a pulsed excitation and readout.

As shown in FIG. 4, the light source(s) may emit a series of pulses with a repetition rate that is adequate for the appreciation of transient phenomena related to the cardiac rhythm. To fix the ideas, without setting limitations to the invention, the cardiac rhythm may be supposed to vary between 40 and 200 bpm, which correspond to a fundamental frequency between 0.67 Hz and 3.3 Hz. The light source may emit pulses at a repetition rate of 150 Hz.

In the example shown, the glucose concentration is measured by the stimulated Raman scattering. Two sources emit light of different frequencies: pump source 60a emits photons at angular frequency $\omega_p$ and Stokes source 60b emits photons a of angular frequency $\omega_S$. When the difference in frequency between both photons $(\omega_p - \omega_S)$ corresponds to that of a specific vibro-rotational transition in the molecule of glucose, the intensity of photons at frequency $\omega_p$ decreases, while the intensity of photons at frequency $\omega_S$ increases accordingly. The signal is resonantly enhanced and is considerably higher than that of the spontaneous Raman scattering. Preferably at least one, possibly both, of sources 60a and 60b are pulsed at a repetition rate high enough to appreciate phenomena related to the cardiac rhythm (plot 66), for example 150 Hz.

If the pump beam 62a and the Stokes beam 62b are absorbed by a glucose solution 17—as in the top part of FIG. 4—the signal 211 collected by the photosensor consists of a series of equal pulses, with a constant attenuation determined by the concentration of the solution 17.

If the glucose solution is replaced by a volume of live irrorated tissue 10, the Raman signal 212 varies according to the instantaneous value of irroration of the tissue and to the glycaemia. Referring to FIG. 4, the intensity of the received Raman signal 212 has a variable component 215 correlated with the cardiac rhythm, on top of a constant or slowly varying background. The logical circuit 52 is programmed to extract a variable component 215 compatible with a cardiac rhythm from the samples 212. The variable component 215 is correlated to the glucose concentration in the pulsatile fraction of blood and its amplitude is used to compute the glycaemia, while the constant component caused by background illumination, random noise, and glucose in the tissues, is discarded.

In another non-illustrated variant, the monochromator 72 is omitted and the dual detectors 41, 42 are replaced by a single wavelength-resolving detection system, generating both the Raman signal and the PPG signal. One could also imagine a compound detector comprising an array of photosensitive pixels, some responding to light in a broad band of wavelengths for the generation of the PPG signal, other responding only to light in the region of interest 105 for the searched analyte. This could be obtained by a mosaic of absorption filters, or by a grating or dispersive device, as already mentioned.

Preferably, the signal generated at the photodetectors is pre-processed by a suitable circuit before being digitized by the ADC 51. This front-end, which is not explicitly represented in the drawing, may be included in the photodetectors or separate, and could implement functions such as analogue amplification, integration, filtering, and baseline subtraction, as the circumstances require. The logic circuit 52 may be arranged to control the parameters of the front-end, for example to implement an automatic gain control or an automatic baseline subtraction.

Importantly, the logic circuit 52 is programmed to extract the amplitude 205 of the PPG signal, by a digital band-pass filter tuned on the expected cardiac frequency or any other suitable processing. This value is determined by the intensity of the excitation source and by the amount of blood present in the sensed region of the body. According to the invention, the amplitude of the PPG signal is used to extract a quantitative determination of analyte concentration from the Raman data, obviating the lack of a calibration with a standardized sample. The logic circuit MCU could determine the concentration as $G \propto I_R / I_P$, where $I_R$ denotes the intensity of the Raman signal and $I_P$ that of the PPG signal.

The intensity of the Raman signal $I_R$ depends from the concentration of glucose in the sample, while the amplitude of the PPG signal is related to the fractional volume of pulsatile blood. Since both signals derive from the incident beam 62, the ratio $I_R / I_P$ between the Raman signal and the PPG signal is largely independent from the variations illumination and optical propagation.

In an embodiment, if the intensity of the Raman signal is sufficient, the logic circuit 52 is programmed to analyse the time variation of the $I_R$ signal and extract a component that is correlated with the time variation of the PPG signal, or has the same frequency as the PPG signal. In this manner, the logic circuit retains only the contribution of the glucose that is contained in the pulsatile blood fraction in the sample 10 and estimates the glycaemia as $G \propto I'_R / I_P$ where $I'_R$ denotes a component of the Raman intensity that is correlated in time with the PPG signal, or has the same frequency.

Figures 5, 6A, 6B, 6C, 6D, 6E, 7, 8:
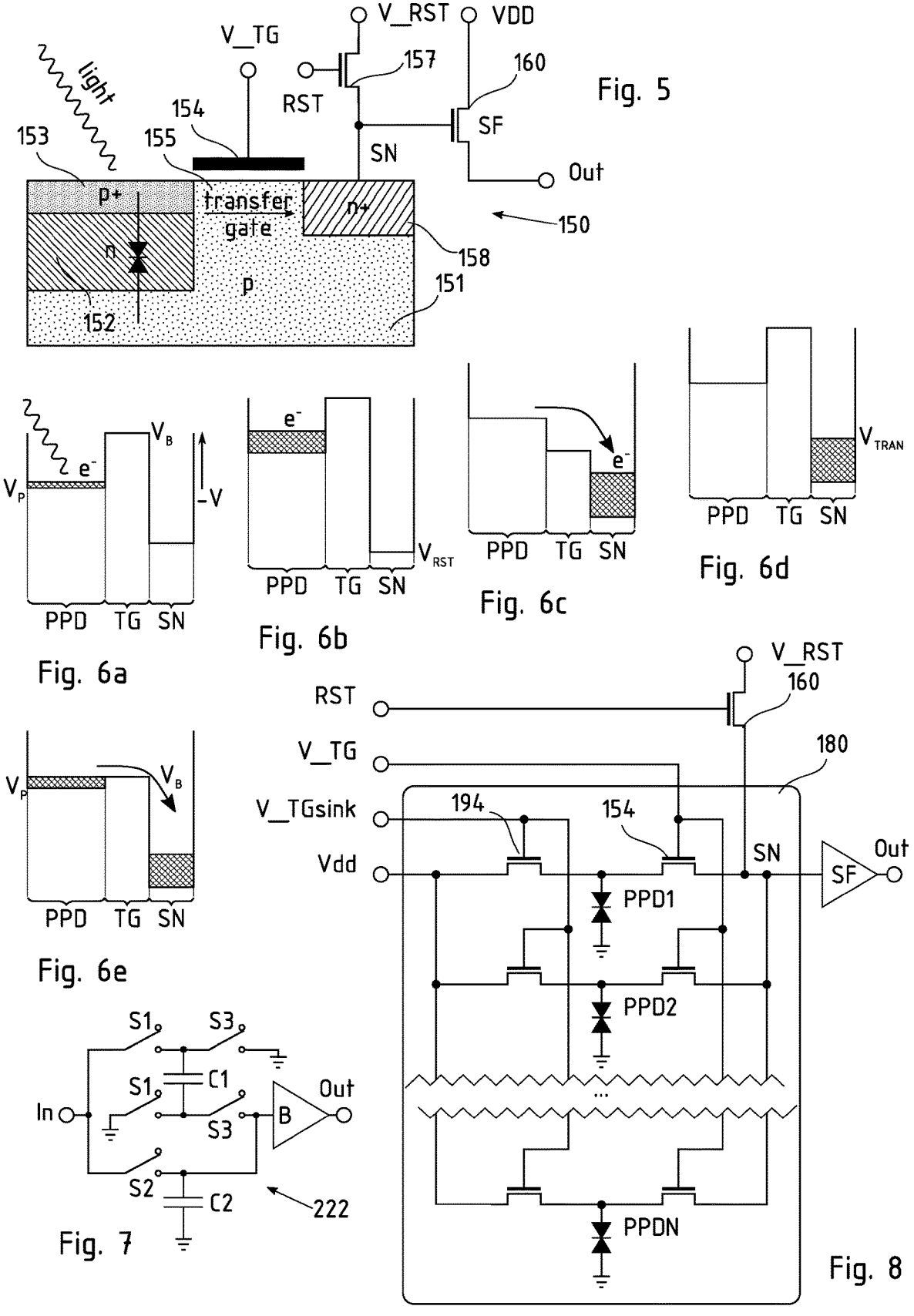
FIG. 5 illustrates schematically a structure of a PPD photosensitive pixel applicable to the present invention.
FIGS. 6*a* to 6*d* illustrate the different potentials and corresponding transfer of carriers in a PPD pixel as that represented in FIG. 5 and in successive phases of operation.
FIG. 6*e* is a variant of FIG. 6*c*.
FIG. 7 is a simplified schematics of a low-power double correlated sampling stage.
FIG. 8 shows a macro-pixel structure.

Several devices can be used for the photodetectors 41 and 42. In a preferred realization, the device of the invention adopts pinned photodiodes (PPD), the main elements whereof are represented schematically in FIG. 5, in a pixel of a CMOS imaging sensor. They include an n-type buried potential well region 152 sandwiched within the lower p layer 151 (that may be tied to the reference potential) and the p+ pinning layer 153. In the depleted state, without any photon-induced carrier, the potential in the well region 152 assumes spontaneously a positive value $V_p$ called the pinning potential, as shown in FIG. 6a. The transfer gate region 155 is a potential barrier whose height can be controlled by the potential V_TG on the gate 154, and the sense node region 158 is a n+ region that can be charged at a predetermined value $V_{RST}$ by the transistor 157 and read by source follower 160. In this and the following figures the p+-n-p structure of the PPD has been indicated with a symbol containing two conventional junction diodes nose-to-nose but, in the literature, such structures are indicated in various ways.

Importantly, and differently form photodiodes and other photodetectors, PPD do not generate a photocurrent proportional to the incident light intensity because, in normal conditions, the photoelectrons collect in the potential well of the n region 152. photoelectrons are stored in the collecting region 152 until the barrier under the transfer gate is lowered by applying a sufficient potential to the gate electrode 154. PPD are inherently integrating devices. Another advantage of the PPD lies in their very low dark currents and shot noise, and excellent performances at low illumination levels.

FIGS. 6a to 6d illustrate a sequence of operations implied in the readout of such a pixel: FIG. 6a shows the integration phase. The cycle starts with the PPD potential well in a depleted state, and the barrier $V_B$ is closed, singe the gate electrode 154 is at a low potential. The impinging radiation is converted in photoelectrons that accumulate in the well.

FIG. 6b shows a reset operation that may take place immediately before or during the integration of FIG. 6a: the transistor 157 momentarily in set in conduction, whereby the sense node is charged to a determined positive potential $V_{RST}$, then left floating.

At the end of the integration phase, the transfer phase shown in FIG. 6c takes place: the potential barrier is momentarily lowered by applying a suitable high potential to the transfer gate electrode 154. The photoelectrons migrate into the sense node at lower potential.

In the readout final phase, visible in FIG. 6*d*, the potential barrier is raised again, and the source follower senses the value $V_{TRAN}$. The integrated charge value is $Q=(V_{TRAN}-V_{RST})\cdot C_{SN}$, where $C_{SN}$ denotes the capacity of the sense node.

Preferably, the source follower 160 performs a correlated double sampling of the potential $V_{RST}$ of the sense node at the reset and the potential $V_{TRAN}$ after the transfer. The difference $V_{TRAN}-V_{RST}$ may be obtained numerically or, better, by a dedicated analogue circuit. Correlated double sampling not only remove the constant $V_{RST}$ value, but also reduces flicker noise.

FIG. 8 shows a simplified schematics of a switched capacitor circuit 222 that may be used, in the scope of the invention, to compute the difference between two consecutive correlated samples. The circuit comprises two capacitors C1, C2 of same value that can be charged separately from the input, by closing momentarily the switches S1, respectively the switch S2, or connected in parallel with opposite polarities, by closing switches S3 and leaving open switches S1 and S2. The switches may be implemented by MOSFETs or in any other way.

In a possible sequence of operations—which is not however the only possible—the input of the double correlating sampling circuit of FIG. 8 may be connected at the output of a pixel and, while the reset switch 160 is closed, the switches S1 may be closed to copy the value $V_{RST}$ into capacitor C1. Successively, after the integration and transfer phases described above, the switch S2 is closed momentarily to copy the value $C_{TRAN}$ into capacitor C2. By opening S1, S2, and closing S3, the capacitors C1, C2 are connected in parallel but the polarity of C1 is reversed: The output of this stage is $(V_{TRAN}-V_{RST})/2$.

Advantageously, the double correlated sampling stage 222 can perform the subtraction of the $V_{RST}$ value in a fast and precise way, with a negligible power consumption, which is of paramount importance in portable and wearable applications. The device of the invention may include several such stages to subtract the reset voltage of the pixels, $V_{RST}$, as illustrated above, or to subtract a background illumination value, or other values as required by data processing. It lends itself to several modifications that may be useful on various situations, for example the values of the capacitors could be chosen to perform a weighted subtraction, and the gain of the output buffer could be different from unity.

FIG. 8 represents a structure of a part of a photodetector device that is used in a preferred embodiment of the present invention. With respect to the pixel of FIG. 5, each pixel has now an additional sink gate 194 between the PPD potential well and a positive voltage source. By this additional sink gate, the storage well of the PPD can be emptied without transferring the charge to the sense node. This may be used to implement an electronic global shutter, for example.

Another improvement of the device of FIG. 8 is that a plurality of PPD are interconnected to form a "macropixel" 180. Each cell of the macropixel has a PPD and two transfer gates, but they all share a same sense node SN and have a source follower and reset transistor in common. The individual pixels in a macropixel are arranged with the control electrodes of all the sink gates interconnected, and all the control electrodes of the transfer gates interconnected, such that the emptying of the storage wells, integration, and transfer phases are simultaneous in all the pixel of the macropixel. This is different from architectures that transfer charge from several pixels to a shared sense node in a rolling fashion.

A macropixel may correspond to a spatially compact cluster of pixels, to row/column of an array, or to any arrangement of pixels in the array, no matter how they are arranged on the surface, electrically connected as shown.

The macropixel disposition of FIG. 8 is advantageous because, the photoelectrons from several individual PPD are transferred to a shared sense node and the macropixel behaves like a single photodetector with a large area, but with the inherent low-noise capabilities of PPDs. Since the pixels are operated synchronously, the integration window can be precisely determined in time.

An interesting variant to the operative cycle of FIGS. 6*a*-6*d*, shown in FIG. 6*e*, consists in adapting the value of the transfer gate voltage V_TG such that the potential barrier is not lowered all the way down, but decreased to a value $V_B<V_P$. In this manner, the potential well of the PPD is emptied only in part. This amounts to subtracting a constant value form $V_{TRAN}$ and can be used to zero a background illumination value, for example. Importantly, the charge left in the potential well is discharged by the sink transistor 194 before the next integration and does not affect successive cycles.

Figure 9:
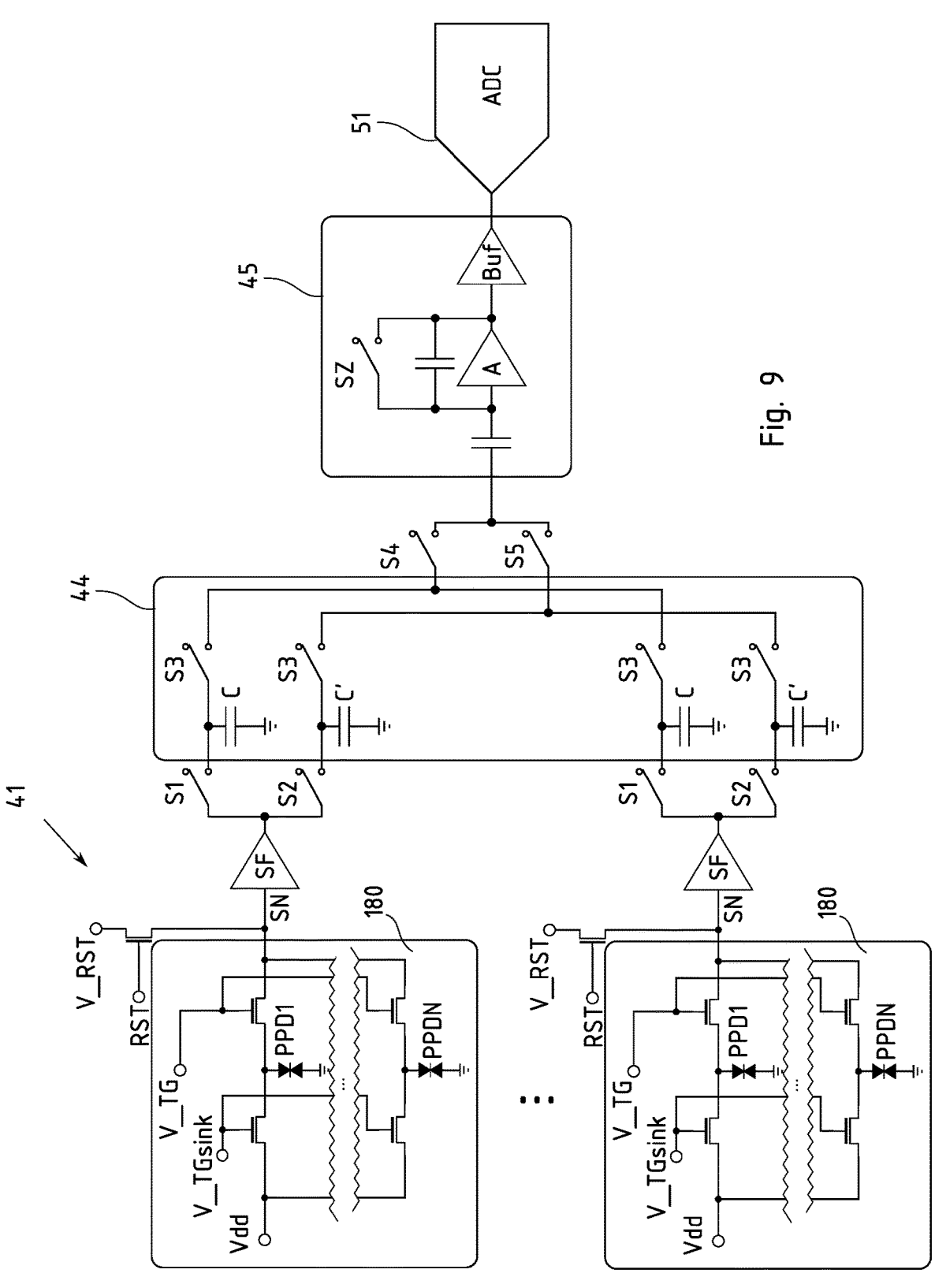
FIG. 9 is one possible arrangement of an electronic circuit designed to process the signal issuing from a plurality of macropixels.

FIG. 9 shows a possible implementation of a PPD photodetector suitable for the realization of the invention in the position of the Raman detector 41 and/or of the PPG detector 42 of FIG. 1. The figure shows also part of the associated readout and digitization electronics, and these sub-circuits may be incorporated totally or in part in the same chip as the photodetectors.

The detector of FIG. 9 comprises a plurality of PPD pixel organized in macropixels as shown in FIG. 7. Each macropixel may correspond to a column of pixels, and there may be as many macropixels as columns, such that the whole photosensitive surface of the array, which may include 100 000 or more individual pixels, is covered.

The macropixels are connected to an averaging stage 44 that collects the charges from each macropixels and averages them. The first sample of each pixel is stored in capacitors C by opening switches S2 and S3 and closing switches S1. Then switches S1 are opened, switches S2 are closed, and the second sample is stored in capacitors C'. The averaging of these samples is performed by closing the switches S3, whereby all the capacitors C, respectively C' are connected in parallel and become, in effect two larger capacitors storing the whole charge of the respective samples. This process allows averaging and multiple sampling at negligible power consumption.

The charge stored in capacitors C is transferred to the sample-and-hold stage 45 by closing momentarily the switch S4 and digitized by the ADC 51. Then, the sample-and-hold is reset by SZ, and the switch S % is closed to sample and digitize the charge stored in capacitors C'.

It is noted that the circuit of the invention reads all the pixels in the macropixels (of the whole array) simultaneously, with consistent timing, and delivers an average illumination value, in contrast with conventional image sensors where the individual pixels are read separately in rolling fashion.

The circuit of FIG. 9 may include double correlated sampling stages as described above in relation to FIG. 7, or functionally equivalent stages, to implement certain subtraction of pedestal values, like a reset voltage $V_{RST}$ or a background illumination value in hardware. This may allow a reduction of the rate of the ADC 51 and, since the power consumption of the double sampling stage of FIG. 7 is very low, leads to a better battery life in portable devices.

REFERENCE SYMBOLS

10 irrorated tissue
17 standard solution
41 Raman photosensor
42 PPG photosensor
44 averager
45 sample-and-hold
51 ADC
52 logic circuit, microcontroller
59 display
60 light source, laser
60a Raman pump source
60b Raman stimulation source
61 illumination optics
62 incident beam
66 light pulses
71 light collection device
72 filter, monocromator
102 Raman spectrum
105 region of interest
150 pixel
151 lower layer
152 storage well
153 pinning layer
154 transfer gate electrode
155 transfer channel
157 reset transistor
158 sense node
160 source follower
180 macropixel
194 sink transistor
202 PPG signal
205 amplitude of the AC component of the PPG signal
211 constant Raman signal
212 time-variable Raman signal
215 pulsatile component of the Raman signal
222 double correlated sampling stage

The invention claimed is:

1. An optical device for in-vivo determination of a concentration of an analyte in blood, comprising:
an optical interface for optical coupling to a sensed region of a body
a light source arranged for transmitting pulsed UV, pulsed visible or pulsed infrared light to the sensed region;
an optical collection system receiving scattered light from the sensed region;
first optical detector, generating a time-variable Raman signal influenced by the concentration of the analyte;
an optical filter placed before the first optical detector and arranged for selecting from the scattered light a spectral component produced in inelastic scattering on molecules of the analyte, wherein the first optical detector generates a time-variable Raman signal proportional to an intensity of said spectral component;
a second optical detector for detecting unfiltered elastically scattered light to generate a time-variable PPG (photoplethysmography) signal from the light from the light source; and
a logic circuit, arranged to determine the concentration of the analyte in the blood in the sensed region based on the time-variable Raman signal and the time-variable PPG signal;

wherein both the elastically scattered light and inelastically scattered light originate from the same light source.

2. The optical device of claim 1, including a photoplethysmography device generating the time-variable PPG signal indicative of an amount of blood present in the sensed region.

3. The optical device of claim 1, wherein the optical device is arranged to acquire an intensity of the unfiltered elastically scattered light from the sensed region and extract from the intensity of the unfiltered elastically scattered optical radiation a periodic time-variable PPG signal corresponding to a cardiac rhythm.

4. The optical device of claim 1, wherein the light source is pulsed, and the first optical detector is read synchronously with pulses of the light source.

5. The optical device of claim 1, wherein the logic circuit is arranged to scale the time-variable Raman signal by the time-variable PPG signal.

6. The optical device of claim 1, wherein the light source is a laser diode or a light-emitting diode and wherein the light source emits in a visible or near-infrared region.

7. The optical device of claim 1, wherein the optical filter includes a wavelength dispersive grating, or an interference filter.

8. The optical device of claim 1, wherein the filter is tuned to let pass wavelengths corresponding to glucose Raman-scattered light.

9. The optical device of claim 1, included in a wearable device, and arranged for providing a continuous or quasi-continuous determination of the concentration of the analyte.

10. The optical device of claim 1, wherein said analyte is glucose.

11. The optical device of claim 1, wherein the optical detector comprises a CMOS integrated circuit with an array of photosensitive pixels, and a circuit for a simultaneous reading of an average illumination value from the array of photosensitive pixels or part of the array of photosensitive pixels.

12. The optical device of claim 1, wherein the sensed region of the body is a wrist.

13. The optical device of claim 1, wherein the sensed region of the body is a finger.

14. The optical device of claim 1, wherein both the first optical detector and the second optical detector are responsive to the light source.

15. The optical device of claim 1, wherein the light source is a vertical-cavity surface-emitting laser (VCSEL) laser.

16. The optical device of claim 1, wherein the light source is a tuneable laser.

17. The optical device of claim 1, wherein the optical filter is tuneable.

18. The optical device of claim 1, wherein the first optical detector and the second optical detector are pinned photodiodes.

19. The optical device of claim 1, wherein the first optical detector and the second optical detector each include an n-type buried potential well within a lower p layer and a p+ pinning layer.

20. The optical device of claim 1, wherein the each of the first optical detector and the second optical detector include a potential well for collecting photoelectrons, a transfer gate for controlling transfer of the photoelectrons from the potential well, and a sense node region for receiving the photoelectrons.

21. The optical device of claim 1, wherein the logic circuit is arranged to determine the concentration as a value proportional to a ratio of the time-variable Raman signal to the time-variable PPG signal.

22. The optical device of claim 1, wherein the logic circuit is arranged to analyze the time variation of the Raman signal to extract a component of the Raman intensity that is correlated in time with the time-variable PPG signal or has the same frequency as the time-variable PPG signal, and to determine the concentration as a value proportional to a ratio of the extracted component to the time-variable PPG signal.

23. A method of noninvasive determination of a concentration of an analyte in a part of a body, comprising:

illuminating a sensed region of the body with an essentially monochromatic visible or infrared light, originating from a light source;

receiving light scattered from the sensed region;

filtering a first portion of the light scattered from the sensed region;

determining an intensity of a component of the scattered light imputable to Raman scattering of the analyte after filtering from the scattered light a spectral component produced in inelastic scattering on molecules of the analyte;

determining from an unfiltered component of the scattered light a time-variable PPG signal imputable to elastic scattering indicative of an amount of blood present in the sensed region; and determining the concentration based on the intensity of said component and on the time-variable PPG signal;

wherein both components of the scattered light originate from the same light source.

24. The method of claim 23, wherein the sensed region of the body is a wrist.

25. The method of claim 23, wherein the sensed region of the body is a finger.

26. An optical device for in-vivo determination of a concentration of an analyte in blood, comprising:

an optical interface for optical coupling to a sensed region of body a pulsed light source arranged for transmitting pulsed UV, pulsed visible or pulsed infrared light to the sensed region;

an optical collection system receiving a scattered light from the sensed region;

a first optical detector, generating a time-variable Raman signal influenced by the concentration of the analyte;

an optical filter placed before the first optical detector for selecting from the scattered light a spectral component produced in inelastic scattering on molecules of the analyte, wherein the first optical detector generates a time-variable Raman signal proportional to an intensity of said spectral component;

a second optical detector for detecting unfiltered elastically scattered light to generate a time-variable PPG (photoplethysmography) signal from the light from the pulsed light source by acquiring an intensity of scattered light from the sensed region and extracting from the intensity of the elastically scattered optical radiation the time-variable PPG signal corresponding to a cardiac rhythm; and a logic circuit, arranged to determine the concentration of the analyte in the blood in the sensed region based on the time-variable Raman signal and the time-variable PPG signal synchronously with pulses of the pulsed light source;

wherein the first optical detector and the second optical detector are embodied in a CMOS integrated circuit with an array of photosensitive pixels, and a circuit for a simultaneous reading of an average illumination value from the array of photosensitive pixels or part of the array of photosensitive pixels, and wherein both the elastically scattered light and inelastically scattered light originate from the same light source.

* * * * *